(12) United States Patent
Nishimura et al.

(10) Patent No.: US 9,351,942 B2
(45) Date of Patent: May 31, 2016

(54) PATCH AND PATCH PREPARATION

(75) Inventors: Masato Nishimura, Ibaraki (JP); Yoshihiro Iwao, Ibaraki (JP); Katsuhiro Okada, Ibaraki (JP); Kensuke Matsuoka, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 183 days.

(21) Appl. No.: 13/983,481

(22) PCT Filed: Feb. 1, 2012

(86) PCT No.: PCT/JP2012/052307
§ 371 (c)(1),
(2), (4) Date: Aug. 2, 2013

(87) PCT Pub. No.: WO2012/105619
PCT Pub. Date: Aug. 9, 2012

(65) Prior Publication Data
US 2013/0315978 A1    Nov. 28, 2013

(30) Foreign Application Priority Data

Feb. 2, 2011    (JP) ................................. 2011-021200

(51) Int. Cl.
*A61K 9/70* (2006.01)
*A61K 31/405* (2006.01)
*A61K 31/663* (2006.01)

(52) U.S. Cl.
CPC .............. *A61K 9/7053* (2013.01); *A61K 31/405* (2013.01); *A61K 31/663* (2013.01); *Y10T 428/2857* (2015.01)

(58) Field of Classification Search
None
See application file for complete search history.

(56) References Cited

U.S. PATENT DOCUMENTS

| 5,508,038 | A * | 4/1996 | Wang et al. ................... 424/448 |
| 2006/0034900 | A1 * | 2/2006 | Saeki et al. ................... 424/448 |
| 2006/0034901 | A1 | 2/2006 | Akemi et al. |
| 2007/0219286 | A1 * | 9/2007 | Ishii ............................. 523/111 |
| 2009/0123526 | A1 | 5/2009 | Kuribayashi |
| 2009/0142388 | A1 | 6/2009 | Inosaka et al. |
| 2010/0119584 | A1 | 5/2010 | Matsuzawa et al. |
| 2013/0310777 | A1 | 10/2013 | Nishimura et al. |

FOREIGN PATENT DOCUMENTS

| CN | 101416955 A | 4/2009 |
| EP | 1 844 773 A1 | 10/2007 |
| EP | 1844773 | * 10/2007 |
| EP | 2 145 632 A2 | 1/2010 |
| JP | 61-155320 A | 7/1986 |
| JP | 61-165321 A | 7/1986 |
| JP | 3-071404 B2 | 11/1991 |
| JP | 2006-075588 A | 3/2006 |
| JP | 2007-039451 A | 2/2007 |
| JP | 2007-269753 A | 10/2007 |
| JP | 2009-114175 A | 5/2009 |
| JP | 2011-012102 A | 1/2011 |
| WO | WO 2006/064576 A1 | 6/2006 |
| WO | WO 2006-093139 A1 | 9/2006 |
| WO | WO 2008-146796 A1 | 12/2008 |
| WO | WO 2012/105620 A1 | 8/2012 |

OTHER PUBLICATIONS

Japanese Patent Office, Notice of Reasons for Refusal in Japanese Patent Application No. 2011-021200 (Nov. 4, 2014).
European Patent Office, Extended European Search Report in European Patent Application No. 12741642.8 (Aug. 1, 2014).
Japanese Patent Office, International Search Report in International Patent Application No. PCT/JP2012/052307 (Mar. 13, 2012).
Chinese Patent Office, First Office Action in Chinese Patent Application No. 201280007446.6 (Sep. 15, 2014).

* cited by examiner

*Primary Examiner* — Bethany Barham
*Assistant Examiner* — Melissa Javier
(74) *Attorney, Agent, or Firm* — Leydig, Voit & Mayer, Ltd.

(57) ABSTRACT

The invention provides a patch and a patch preparation having an adhesive layer with a high adhesive force, wherein the hydrophobic adhesive layer does not bloom even when an organic fluid component having high polarity is contained therein. The patch contains a support and an adhesive layer on at least one surface of the support, wherein the adhesive layer contains a synthetic rubber having a viscosity average molecular weight of 1,700,000-6,500,000, an organic fluid component having high polarity, a tackifier, and magnesium aluminometasilicate. In the patch preparation, the above-mentioned adhesive layer further contains a drug.

8 Claims, No Drawings

PATCH AND PATCH PREPARATION

CROSS-REFERENCE TO RELATED APPLICATIONS

This patent application is the U.S. national phase of International Patent Application No. PCT/JP2012/052307, filed Feb. 1, 2012, which claims the benefit of Japanese Patent Application No. 2011/021200, filed on Feb. 2, 2011, which are incorporated by reference in their entireties herein.

TECHNICAL FIELD

The present invention relates to a patch and a patch preparation, comprising a support and an adhesive layer provided on at least one surface of the support.

BACKGROUND ART

Conventionally, various patches and patch preparations have been developed to protect the skin, administer a drug into the body through skin surface and the like.

Since synthetic rubbers used as an adhesive for an adhesive layer of a patch preparation do not have a functional group, they are preferable in view of the stability of a drug in the adhesive layer, and advantageously show good drug releasability. However, due to the absence of a functional group, such synthetic rubbers are hydrophobic and, when an organic fluid component having high polarity is added to an adhesive layer, its low compatibility with the organic fluid component poses problems. That is, when the compatibility of the synthetic rubber and the organic fluid component is low, the organic fluid component blooms on the adhesive surface. As a result, the adhesive force decreases and the patch preparation adhered to an adhesion object is detached soon. Therefore, when an adhesive layer using a synthetic rubber as an adhesive is added with an organic fluid component in an attempt to impart a soft feeling to the adhesive layer, and reduce pain and irritation due to the skin adhesive force produced when detaching the patch preparation from the skin, only an organic fluid component having low polarity can be used as the organic fluid component, which also limits the drug to one with low polarity.

Examples of the documents aiming at resolution of the problem that occurs when adding a component having low compatibility with the adhesive to the adhesive layer include the following.

Patent document 1 discloses a patch preparation containing an adhesive, a hardly water-soluble drug, 3 kinds of organic fluid components for dissolution of the hardly water-soluble drug, and cross-linked polyvinyl pyrrolidone. Here, cross-linked polyvinyl pyrrolidone is added to maintain, in the adhesive layer, an organic fluid component having high polarity and low compatibility with the rubber-based adhesive. It is described that, in Comparative Example in which the adhesive layer does not contain cross-linked polyvinyl pyrrolidone, an organic fluid component bloomed from the adhesive layer and the adhesive force was not measured.

Patent document 2 discloses a hydrous adhesive composition containing polybutene, a non-ionic surfactant, and an oil-absorbing inorganic powder. This document describes that bleeding of hydrophobic polybutene from the hydrophilic hydrous adhesive composition was solved by the oil-absorbing inorganic powder. However, this document is completely silent on the bleeding of an organic fluid component having high polarity from an adhesive layer using a hydrophobic adhesive such as synthetic rubber and a method of solving the bleeding.

As a patch preparation containing magnesium aluminometasilicate in an adhesive layer, for example, patent document 3 describes a patch preparation obtained by extending a plaster containing an A-B-A type thermoplastic elastomer, an alicyclic saturated hydrocarbon resin, liquid paraffin, an efficacy component, and magnesium aluminometasilicate. However, this document merely refers to a method of suppressing a decrease in the cohesive force of a plaster (adhesive layer).

DOCUMENT LIST

Patent Documents patent document 1: JP-A-2009-114175
patent document 2: JP-A-2007-39451
patent document 3: JP-B-3-71404

SUMMARY OF THE INVENTION

Problem to be Solved by the Invention

The problem to be solved by the present invention is to provide a novel patch and a patch preparation, which are provided with an adhesive layer affording a sufficiently high adhesive force even when the adhesive layer contains a highly hydrophobic adhesive such as synthetic rubber together with an organic fluid component having high polarity which is less compatible with the highly hydrophobic adhesive.

Means of Solving the Problem

The present inventors have conducted intensive studies in an attempt to solve the aforementioned problem and found that an organic fluid component having high polarity and less compatible with a highly hydrophobic adhesive can be maintained in an adhesive layer when the adhesive layer contains magnesium aluminometasilicate together with the highly hydrophobic adhesive such as synthetic rubbers, and further studies based on such finding resulted in the completion of the present invention.

Accordingly, the present invention provides the following.
[1] A patch comprising a support and an adhesive layer on at least one surface of the support, wherein
the adhesive layer comprises a synthetic rubber having a viscosity average molecular weight of 1,700,000-6,500,000, an organic fluid component having high polarity, a tackifier, and magnesium aluminometasilicate.
[2] The patch of the above-mentioned [1], wherein the organic fluid component having high polarity has an angle within the range of 20°-80° as calculated by the following formula using an inorganic value and an organic value in an organic conceptual diagram:

$$\text{Angle}[°] = \arctan(\text{organic value/inorganic value})^{-1} \times (180/\pi)$$

[3] The patch of the above-mentioned [1] or [2], wherein the content of the organic fluid component having high polarity in the adhesive layer is not more than 20 wt % relative to the total weight of the adhesive layer.
[4] The patch of any of the above-mentioned [1]-[3], further comprising an organic fluid component having low polarity which shows lower polarity than the organic fluid component having high polarity.

[5] The patch of the above-mentioned [4], wherein the organic fluid component having low polarity has an angle within the range of 0°-19° as calculated by the following formula and using an inorganic value and an organic value in an organic conceptual diagram:

$$\text{Angle}[°]=\arctan(\text{organic value}/\text{inorganic value})^{-1} \times (180/\pi)$$

[6] The patch of the above-mentioned [4] or [5], wherein the total content of the organic fluid component having high polarity and the organic fluid component having low polarity in the adhesive layer is not more than 50 wt % relative to the total weight of the adhesive layer.
[7] The patch of any of the above-mentioned [1]-[6], wherein the total content of magnesium aluminometasilicate in the adhesive layer is less than 25 wt % relative to the total weight of the adhesive layer.
[8] A patch preparation further comprising a drug in the adhesive layer of the patch of any of the above-mentioned [1]-[7].

Effect of the Invention

According to the present invention, a patch and a patch preparation, which can prevent blooming of an organic fluid component having high polarity on an adhesive layer surface, and afford sufficiently high adhesive force, even if they contain a highly hydrophobic adhesive such as synthetic rubber together with an organic fluid component having high polarity which is incompatible with the synthetic rubber (hereinafter to be also referred to as "organic fluid component having high polarity"), can be realized.

DESCRIPTION OF EMBODIMENTS

The present invention is explained in the following by referring to the embodiments thereof.

The patch of the present invention has an adhesive layer on at least one surface of a support and the adhesive layer contains at least a synthetic rubber having a viscosity average molecular weight of 1,700,000-6,500,000, an organic fluid component having high polarity, a tackifies and magnesium aluminometasilicate.

The patch preparation of the present invention further contains a drug in an adhesive layer of the patch of the present invention.

[Synthetic Rubber]

The first synthetic rubber to be used in the present invention is a synthetic rubber having a viscosity average molecular weight of 1,700,000-6,500,000 (hereinafter to be also referred to as "the first synthetic rubber"), and is not particularly limited as long as the viscosity average molecular weight falls within this range. Specific examples of the synthetic rubber include polydimethyl siloxane, butyl rubber, ethylene-vinylacetate copolymer, ethylene-ethylacrylate copolymer, poly(alkylvinylether) (e.g., poly(propylvinylether), poly(isopropylvinylether), poly(butylvinylether) etc.), poly(2-methylpropene), poly(ethylethylene), poly(1,2-dimethylethylene), ethylethylene-1,2-dimethylethylene copolymer, polyisoprene, polybutadiene, styrene-isoprene-styrene block copolymer, styrene-butadiene-styrene block copolymer and the like. Any one or more kinds of these can be used in combination. Of these, branched aliphatic hydrocarbon polymers such as poly(2-methylpropene), poly(ethylethylene), poly(1,2-dimethylethylene), ethylethylene-1,2-dimethylethylene copolymer and the like are preferable, and poly(2-methylpropene) is particularly preferable, from the cost, handling property and the like.

Since synthetic rubbers have a viscosity average molecular weight of not less than 1,700,000, they have long molecular chains entangled in complexity, and are superior in shape retention of an organic fluid component. Therefore, an adhesive layer containing such synthetic rubber can retain an organic fluid component in an amount exceeding 20 wt % (i.e., more than 20 wt %, preferably not less than 25 wt %, relative to the total weight of the adhesive layer). When the viscosity average molecular weight of the synthetic rubber is less than 1,700,000, the synthetic rubber shows a decreased capacity to maintain the organic fluid component of the synthetic rubber, and therefore, when an organic fluid component is contained in an amount exceeding 20 wt %, the organic fluid component may ooze out from the adhesive layer. Even when the organic fluid component does not ooze out, the adhesive power of the adhesive layer may decrease and a patch preparation adhered to an adhesion object may be detached. On the other hand, when the viscosity average molecular weight of the synthetic rubber exceeds 6,500,000, an adhesive layer containing such synthetic rubber tends to decrease in the skin adhesive force and tackiness.

The first synthetic rubber preferably has a viscosity average molecular weight of 1,700,000-5,500,000, more preferably 2,000,000-5,000,000.

The viscosity average molecular weight here is obtained by calculating the Staudinger index ($J_0$) according to the Schulz-Blaschke equation from the flow time of capillary of the Ubbelohde's viscometer at 20° C., and applying the $J_0$ value to the following equations.

$$J_0=\eta_{sp}/c(1+0.31\eta_{sp})\text{cm}^3/\text{g(Schulz-Blaschke equation)}$$

$$\eta_{sp}=t/t_0-1$$

t: flow time of solution (according to Hagenbach-couette correction)
$t_0$: flow time of solvent (according to Hagenbach-couette correction)
c: concentration of solution (g/cm$^3$)

$$J_0=3.06\times10^{-2}Mv^{0.65}$$

Mv: viscosity average molecular weight

While the content of the first synthetic rubber in the adhesive layer is not particularly limited, it is preferably 5-50 wt %, more preferably 7-45 wt %, particularly preferably 10-40 wt %, relative to the total weight of the adhesive layer.

When the content of the first synthetic rubber in the adhesive layer is less than 5 wt %, the internal cohesive force of the adhesive layer may decrease, and when it exceeds 50 wt %, the adhesive layer may become hard and the tackiness may decrease.

When desired, the adhesive layer may further contain a synthetic rubber having a viscosity average molecular weight of 40,000-85,000 (hereinafter to be also referred to as "the second synthetic rubber") besides the first synthetic rubber. Since the second synthetic rubber shows high flowability as compared to the first synthetic rubber, the use of the first synthetic rubber and the second synthetic rubber in combination suppresses separation of the first synthetic rubber, which is easily separable due to the low affinity, from a tackifier, whereby the adhesive layer can maintain adequate flexibility.

When the viscosity average molecular weight of the second synthetic rubber is less than 40,000, the affinity of the tackifier and the second synthetic rubber becomes too high. Therefore, the affinity of the tackifier and the first synthetic rubber may decrease and separation thereof may not be sufficiently suppressed. When the viscosity average molecular weight of the second synthetic rubber exceeds 85,000, the affinity of the second synthetic rubber and the first synthetic rubber becomes too high. Therefore, the affinity of the tackifier and the first synthetic rubber may decrease and they may be separated.

Specific examples (rubber kind) of the second synthetic rubber include those similar to the specific examples of the aforementioned first synthetic rubber, and one or more kinds thereof can be used. While the first synthetic rubber and the second synthetic rubber may be homogeneous or heterogeneous, they are preferably homogeneous in view of the compatibility thereof.

While the content of the second synthetic rubber in the adhesive layer is not particularly limited, it is preferably 5-50 wt %, more preferably 7-45 wt %, most preferably 10-40 wt %, relative to the total weight of the adhesive layer. When the content of the second synthetic rubber in the adhesive layer is less than 5 wt %, the separation of the first synthetic rubber and the tackifier may not be sufficiently suppressed, and when it exceeds 50 wt %, the internal cohesive force of the adhesive layer may decrease.

When desired, a third synthetic rubber having a viscosity average molecular weight smaller than that of the first synthetic rubber and larger than that of the second synthetic rubber may be added to the adhesive layer. Examples of the third synthetic rubber include those similar to the examples recited for the above-mentioned first synthetic rubber, and one or more kinds thereof can be used.

[Organic Fluid Component Having High Polarity]

The organic fluid component having high polarity in the present invention (hereinafter to be also referred to as "the first organic fluid component") is fluid at room temperature (25° C.) (when two or more kinds are mixed, the mixture is fluid room temperature (25° C.)), and means an organic substance incompatible with the first synthetic rubber.

Here, being "incompatible with the first synthetic rubber" means that, when an organic fluid component (1 part by weight) and the first synthetic rubber (9 parts by weight) are mixed in the presence of an organic solvent compatible therewith (for example, toluene etc.) (50 parts by weight) until they become uniform, the aforementioned organic solvent is dried and removed and the obtained solid is preserved at room temperature (25° C.) for 1 week, bleeding of the organic fluid component having high polarity can be confirmed by visual observation. The mixing of the organic fluid component and the first synthetic rubber in the presence of the above-mentioned organic solvent is performed by, for example, manually stirring an organic fluid component, the first synthetic rubber and an organic solvent with a spatula for 30 min.

Such organic fluid component having high polarity and incompatible with the first synthetic rubber is specifically an organic fluid having an angle within the range of 20°-80° as calculated by the following formula using an inorganic value and an organic value in an organic conceptual diagram (hereinafter this angle is also referred to as "angle on organic conceptual diagram") (i.e., organic compound which is fluid at room temperature (25° C.)).

$$\text{Angle}[°]=\arctan(\text{organic value}/\text{inorganic value})^{-1}\times(180/\pi)$$

In the organic conceptual diagram, the properties of a compound are divided into organic value showing a covalent bond type (hydrophobicity) and inorganic value showing ionic bond type (hydrophilicity), and any organic compound is plotted on orthogonal coordinates with the organic value on the x-axis, and the inorganic value on the Y-axis. The organic conceptual diagram is explained in detail in "New edition Organic Conceptual Diagram Foundation and Application" (YOSHIO KOUDA, YOSHIRO SATOU, YOSHIO HONMA, new edition, SANKYO PUBLISHING, Nov. 30, 2008). In general, the closer to the organic axis, the higher the hydrophobicity, and the closer to the inorganic axis, the higher the hydrophilicity.

Examples of the organic fluid having an angle on the organic conceptual diagram of 20°-80° include glycols such as glycerol, ethylene glycol, diethylene glycol, propylene glycol, dipropyleneglycol, tripropyleneglycol, triethylene glycol, polyethylene glycol, polypropylene glycol and the like; non-ionic surfactants such as castor oil polyethoxylated hydrogenated derivative (castor oil polyethoxylated hydrogenated 40, castor oil polyethoxylated hydrogenated 50, castor oil polyethoxylated hydrogenated 60 etc.), polyoxyethylene sorbitan fatty acid esters (polysorbate 80 (Tween80), polysorbate 60 (Tween60), polysorbate 40 (Tween40), polysorbate 20 (Tween20) etc.), polyoxyethylene polyoxypropylene glycol (pluronic F-68, PEP-101, poloxamer 188 etc.) and the like; anionic surfactants such as sodium lauryl sulfate and the like; hydroxy acids such as lactic acid, glycolic acid, malic acid, tartaric acid, citric acid and the like; fatty acids such as acetic acid, capric acid, caprylic acid, lauric acid, oleic acid and the like; glycerin middle-chain fatty acid esters oleic acid, caprylic acid, lauric acid and the like (monoglyceride, diglycerides, triglyceride or a mixture thereof); esters such as ethyl lactate, cetyl lactate, triethyl citrate, dibutyl phthalate, benzyl acetate and the like; $C_1$-$C_{14}$ monohydric alcohols such as saturated alcohols (e.g., methanol, ethanol, straight chain or branched chain propanol, straight chain or branched chain butanol, straight chain or branched chain pentanol, straight chain or branched chain hexanol, straight chain or branched chain heptanol, straight chain or branched chain octanol, straight chain or branched chain nonanol, straight chain or branched chain decanol, straight chain or branched chain undecanol, straight chain or branched chain dodecanol, straight chain or branched chain tetradecanol and the like), and unsaturated alcohols (e.g., straight chain or branched chain propenol, straight chain or branched chain butenol, straight chain or branched chain pentenol, straight chain or branched chain hexenol, straight chain or branched chain heptenol, straight chain or branched chain octenol, straight chain or branched chain nonenol straight chain or branched chain decenol, straight chain or branched chain undecenol, straight chain or branched chain dodecenol and the like); pyrrolidone such as N-methylpyrrolidone, N-dodecylpyrrolidone; sulfoxides such as dimethyl sulfoxide, decylmethyl sulfoxide; 1,3-butanediol; ethoxylated stearyl alcohol and the like.

The first organic fluid component preferably shows the angle on the organic conceptual diagram of 25°-60°, particularly from the aspects of drug permeation acceleration effect of the skin patch preparation.

One or more kinds of the first organic fluid components can be used, and the content thereof in the adhesive layer is preferably 1-20 wt %, more preferably 2-17 wt %, particularly preferably 2-15 wt %, relative to the total weight of the adhesive layer.

[Low Polarity Organic Fluid Component]

The adhesive layer can contain an organic fluid component having low polarity which has polarity lower than that of the first organic fluid component (hereinafter to be also referred to as "the second organic fluid component"). Such second organic fluid component is not particularly limited as long as it is an organic fluid having an angle on the organic conceptual diagram of 0°-19°. Examples thereof include fats and oils such as olive oil, castor oil, lanolin and the like; hydrocarbons such as squalane, liquid paraffin and the like; higher fatty acid alkylester (i.e. an ester of $C_{8-18}$ (preferably $C_{12-16}$) fatty acid with $C_{1-22}$ monohydric alcohol such as isopropyl myristate, isopropyl palmitate, ethyl oleate, isostearyl laurate, octyldodecyl myristate, octyl palmitate and the like, etc.); higher alcohol (i.e. $C_{16-22}$ alcohol such as straight chain alcohol (cetyl alcohol, stearyl alcohol, behenyl alcohol, oleyl alcohol, cetostearyl alcohol, hydrogenated rapeseed oil alcohol etc.), branched chain alcohol (lanolin alcohol, cholesterol, phytosterol, hexyldodecanol, isostearyl alcohol, octyldodecanol etc.) and the like, etc.) and the like. One or more kinds of the organic fluid component having low polarity (the second organic fluid component) can be used.

The content of the second organic fluid component in the adhesive layer is preferably 0-19 wt %, more preferably 7.5-18.75 wt %, particularly preferably 12.5-18.75 wt %, relative to the total weight of the adhesive layer.

When both the first organic fluid component and the second organic fluid component are contained, and when the total content thereof in the adhesive layer is too high, the shape of the adhesive layer becomes difficult to retain. While the content is not particularly limited as long as the shape of the adhesive layer can be maintained, it is preferably not more than 50 wt % of the total weight of the adhesive layer. Since skin permeation and drug dissolution of the drug in the patch preparation are improved as the amount of the organic fluid component that can be retained becomes higher, the total content of the first organic fluid component and the second organic fluid component is preferably more than 20 wt %, more preferably not less than 25 wt %, of the total weight of the adhesive layer.

[Magnesium Aluminometasilicate]

Magnesium aluminometasilicate is an additive conventionally used in the drug pharmaceutical field for the purpose of improving the filling performance and tableting property of powder and granules, and the like. Magnesium aluminometasilicate is available under the trade name of, for example, Neusilin from Fuji Chemical Industry. In addition, magnesium aluminometasilicate is preferably an amorphous composite oxide of aluminum, magnesium and silicon atom, which are three-dimensionally polymerized via an oxygen atom. Such composite oxide is more specifically magnesium aluminometasilicate represented by the formula: $Al_2O_3/aMgO/bSiO_2.nH_2O$ wherein a=0.3-3 and b=0.3-5. Due to its porous structure, such magnesium aluminometasilicate can stably maintain the first organic fluid component with high polarity.

The content of magnesium aluminometasilicate in the adhesive layer can be appropriately set and is not particularly limited. It is preferably not less than 1 wt % and less than 25 wt % relative to the total weight of the adhesive layer. When it is not less than 25 wt %, the adhesive layer becomes too hard, and the adhesive force may decrease markedly. When it is not less than 1 wt %, a sufficient effect can be afforded. That is, an organic fluid component having high polarity and incompatible with the first synthetic rubber (the first organic fluid component) can be maintained in the adhesive layer. The content of magnesium aluminometasilicate is more preferably 2.5-22.5 wt %, still more preferably 5-22.5 wt %, particularly preferably 7.5-22 wt %, most preferably 10-22 wt %.

[Tackifier]

Examples of the tackifier include polybutenes, rosin resin, terpene-based resin, petroleum-based resin (e.g., petroleum-based aliphatic hydrocarbon resin, petroleum-based aromatic hydrocarbon resin, petroleum-based aliphatic-aromatic copolymerization hydrocarbon resin, petroleum-based alicyclic hydrocarbon resin (hydrogenated aromatic hydrocarbon resin) etc.), chroman resin and the like. It is preferably petroleum-based alicyclic hydrocarbon resin (hydrogenated aromatic hydrocarbon resin). One or more kinds of tackifiers may be used in combination. The proportion of the tackifier in the adhesive layer is preferably 5-50 wt %, more preferably 7-45 wt %, particularly preferably 10-40 wt %, relative to the total weight of the adhesive layer. When the proportion of the tackifier is less than 5 wt %, the tackiness may be poor, and when it exceeds 50 wt %, the adhesive layer unpreferably tends to be destroyed and the like.

[Drug]

The drug to be used for the patch preparation of the present invention is not particularly limited, and a transdermally absorbable drug, which can be administered to mammals such as human and the like through the skin, is preferable. Specific examples of such drug include general anesthetics, hypnotic sedatives, antiepileptic drugs, antipyretic analgesic antiphlogistic drugs, anti-vertiginous drugs, psychoneurotic drugs, central neurological drug, antidementia, topical anesthetics, skeletal muscle relaxants, autonomic drugs, antispasmodic drugs, anti-parkinsonian drugs, anti-histamine drugs, cardiac stimulants, drugs for arrhythmia, diuretic, hypotensive drug, vasoconstrictor, coronary vasodilator, peripheral vasodilators, arteriosclerosis drugs, drugs for circulatory organ, anapnoics, antitussive expectorant, hormone drugs, external drugs for purulent diseases, analgesic-antipruritic-styptic-antiinflammatory drugs, drugs for parasitic skin diseases, hemostatic drugs, gout treatment drugs, drugs for diabetes, anti-malignant tumor agents, antibiotic, chemical therapy agents, narcotic, quit smoking aids and the like.

The drug includes not only drugs in the form of a free base, but also physiologically acceptable salts thereof. While such salt is not particularly limited, examples thereof include, but are not limited to, formate, acetate, lactate, adipate, citrate, tartrate, methanesulfonate, fumarate, maleate and the like, and examples of acid addition salts with inorganic acid include hydrochloride, sulfate, nitrate, phosphate and the like. The drug may be a solvate, a hydrate or a non-hydrate.

In the patch preparation of the present invention, a drug having an angle on the organic conceptual diagram of 20°-80° is preferable, and a drug having an angle on the organic conceptual diagram of 22°-79° is more preferable. Such drug is compatible with an organic fluid component having high polarity (the first organic fluid component), and therefore, it is maintained stably in the adhesive layer. While the content of the drug in the adhesive layer is not particularly limited as long as it affords the effect of the transdermal drug and does not impair the adhesion property of the adhesive layer, it is preferably 0.1-50 wt %, more preferably 0.5-40 wt %, relative to the total weight of the adhesive layer. When it is less than 0.1 wt %, the treatment effect may be insufficient, and when it exceeds 50 wt %, the proportion of the adhesive in the adhesive layer becomes too small and the adhesive layer may not show a sufficient adhesive force.

While the support to be used in the present invention is not particularly limited, a support substantially having impermeability to the constituent component (particularly organic fluid component) of the adhesive layer and, particularly in a patch preparation, a support that does not permit a drug in the adhesive layer to pass through the support and be lost from the back face thereof to decrease the content thereof is preferable. Examples of such support include single films such as polyester, nylon, saran (registered trade mark), polyethylene, polypropylene, polyvinyl chloride, ethylene-ethyl acrylate copolymer, polytetrafluoroethylene, Surlyn (registered trade mark) and the like, metal foil, a laminate film of two or more kinds of films selected therefrom and the like. The thickness of the support is preferably 2-100 µm, more preferably 2-50 µm.

The patch and the patch preparation of the present invention preferably have a release liner laminated on the adhesive face until use so that the adhesive face of the adhesive layer can be protected. The release liner is not particularly limited as long as it permits a peel treatment and can ensure a sufficiently light release force. For example, a release liner obtained by subjecting a substrate made of a plastic film formed from one or more kinds of plastic selected from a group consisting of polyester (e.g., poly(ethylene terephthalate) etc.), polyvinyl chloride, polyvinylidene chloride fine paper, paper such as glassine paper and the like; or a laminate film wherein fine paper or glassine and the like and a polyolefin film etc. are laminated, to a peel treatment by applying a silicone resin, fluororesin and the like to a surface of the substrate to be in contact with the adhesive layer is used. From the aspects of barrier property and cost, a release liner having a substrate made from a polyester (particularly, poly(ethylene terephthalate)) film is preferable. The thickness of the release liner is generally 10-200 µm, preferably 25-100 µm.

The shape of the patch and the patch preparation of the present invention is not particularly limited and includes, for example, a sheet, a film, a reservoir type and the like.

The patch and the patch preparation of the present invention can be produced by, for example, dissolving the first synthetic rubber, an organic fluid component having high polarity (the first organic fluid component), a tackifier and magnesium aluminometasilicate (further, a drug in the patch preparation) together with other components added as necessary in a suitable solvent such as toluene and the like, dispersing magnesium aluminometasilicate, applying the obtained coating liquid of a composition for forming an adhesive layer onto a release liner, drying same to form an adhesive layer, and laminating a support on the adhesive layer.

In addition, the patch and the patch preparation of the present invention can be produced by, for example, directly applying the above-mentioned coating liquid of a composition for forming an adhesive layer to a support, and drying same to form an adhesive layer on a support.

The patch and the patch preparation of the present invention can be used by peeling off the release liner immediately before use and adhering the exposed adhesive face to a skin surface and the like.

EXAMPLES

While the present invention is explained in more detail in the following by referring to Examples, the present invention is not limited to the Examples described below. Unless particularly indicated, the proportion of each component is shown in parts by weight.

The starting materials used in Examples and Comparative Examples and abbreviations thereof are as described below.
(Adhesive Component)

Polyisobutylene having a viscosity average molecular weight of 4,000,000 (24 parts) as the first synthetic rubber, polyisobutylene having a viscosity average molecular weight of 55,000 (36 parts) as the second synthetic rubber, and alicyclic saturated hydrocarbon resin (manufactured by Arakawa Chemical Industries, Ltd., ARKON P100) (40 parts) as a tackifier were mixed to give an adhesive component.

(Organic Fluid Component Having High Polarity)
PGML: propylene glycol monolaurate, angle on the organic conceptual diagram 28°
Tween80: polyoxyethylene(20)sorbitan monooleate (manufactured by Wako Pure Chemical Industries, Ltd.), angle on the organic conceptual diagram 56°
Glycerin: glycerin, angle on the organic conceptual diagram 79°
(Organic Fluid Component Having Low Polarity)
IPM: isopropyl myristate (angle on the organic conceptual diagram 10°)
(Magnesium Aluminometasilicate)
Neusilin: NeusilinUFL2 (manufactured by FUJI CHEMICAL INDUSTRY CO., LTD.)
(Powder Other than Magnesium Aluminometasilicate)
XPVP: cross-linked polyvinyl pyrrolidone (BASF, Kollidon CL-M)
$SiO_2$: Sylysia 730 (manufactured by Fuji Silysia Chemical Ltd.)
HT: hydrotalcite (manufactured by Wako Pure Chemical Industries, Ltd.)

Examples 1-30 and Comparative Examples 1-8

Using PGML (angle on organic conceptual diagram 28°) as an organic fluid component having high polarity and according to the compounding ratios described in Table 1, a solution of the composition for forming an adhesive layer in toluene was prepared, the obtained solution was applied onto a poly(ethylene terephthalate) (PET) liner (thickness 75 µm) that underwent a silicone peel treatment such that the thickness after drying was 60 µm, and dried in a hot air circulation type drying device at 100° C. for 3 min to form an adhesive layer. The adhesive layer was adhered to a support made from PET to give a sheet-like patch. The obtained patch was subjected to the following adhesive force test.
[Adhesive Force Test]

A test plate (stainless plate) was uniformly ground on the surface with #360 waterproof abrasive paper, and washed. Thereafter, a 180° tensile test was performed according to the following procedure.
(1) One end in the length direction of a patch (sample) (24 mm width, 50 mm length) was detached in about 5 mm and folded back at an angle of 180°, and auxiliary paper was adhered to extend the length.
(2) The liner was removed, the sample was rapidly adhered to the stainless plate, and a 2-Kg rubber roller was immediately passed twice over the sample at 300 mm/min.
(3) The test plate adhered with the above-mentioned sample was left standing at 23±2° C., relative humidity 50±10% for 30 min.
(4) A 180° tensile jig was mounted on a tensile tester, the test plate was set on the jig, one end of the auxiliary paper was tightly held by the upper grip and continuously peeled off at 300 mm per 1 min, and the load was measured and recorded.
(5) The load was readout 3 times at an equal distance (readout positions: 20, 40, 60 mm) from the chart of the measurement results, and averaged. An average value of N=3 was calculated.
(Evaluation)
xx: Uniform adhesive layer could not be formed due to separation of the toluene solution of the adhesive layer-forming composition and the organic fluid component having high polarity, or coagulation of powder.

x: The adhesive layer was formed and adhered to a support made from PET, but adhesive force could not be measured due to the absence of anchorage to the support.
Δ: adhesive force is less than 0.2[N]
ΔΔ: adhesive force is not less than 0.2[N], less than 0.4[N]
ΔΔΔ: adhesive force is not less than 0.4[N], less than 0.7[N]

◯: adhesive force is not less than 0.7[N], less than 1.0[N]

◯◯: adhesive force is not less than 1.0[N], less than 1.6[N]

☉: adhesive force is not less than 1.6[N], less than 2.0[N]

☉☉: adhesive force is not less than 2.0[N]

TABLE 1

| | | PGML (angle on organic conceptual diagram 28°) was used as organic fluid component having high polarity | | | | |
|---|---|---|---|---|---|---|
| | | organic fluid components | | | powder | |
| — | adhesive | organic fluid component having high polarity PGML | organic fluid component having low polarity IPM | total amount of organic fluid component | magnesium alumino-metasilicate (Neusilin) | other powder |
| Comp. Ex. 1 | 70.0 | 2.5 | 27.5 | 30.0 | 0.0 | — |
| Comp. Ex. 2 | 70.0 | 5.0 | 25.0 | 30.0 | 0.0 | — |
| Comp. Ex. 3 | 70.0 | 10.0 | 20.0 | 30.0 | 0.0 | — |
| Comp. Ex. 4 | 70.0 | 15.0 | 15.0 | 30.0 | 0.0 | — |
| Comp. Ex. 5 | 70.0 | 20.0 | 10.0 | 30.0 | 0.0 | — |
| Ex. 1 | 67.5 | 2.5 | 27.5 | 30.0 | 2.5 | — |
| Ex. 2 | 67.5 | 5.0 | 25.0 | 30.0 | 2.5 | — |
| Ex. 3 | 67.5 | 10.0 | 20.0 | 30.0 | 2.5 | — |
| Ex. 4 | 67.5 | 15.0 | 15.0 | 30.0 | 2.5 | — |
| Ex. 5 | 67.5 | 20.0 | 10.0 | 30.0 | 2.5 | — |
| Ex. 6 | 65.0 | 2.5 | 27.5 | 30.0 | 5.0 | — |
| Ex. 7 | 65.0 | 5.0 | 25.0 | 30.0 | 5.0 | — |
| Ex. 8 | 65.0 | 10.0 | 20.0 | 30.0 | 5.0 | — |
| Ex. 9 | 65.0 | 15.0 | 15.0 | 30.0 | 5.0 | — |
| Ex. 10 | 65.0 | 20.0 | 10.0 | 30.0 | 5.0 | — |
| Ex. 11 | 60.0 | 2.5 | 27.5 | 30.0 | 10.0 | — |
| Ex. 12 | 60.0 | 5.0 | 25.0 | 30.0 | 10.0 | — |
| Ex. 13 | 60.0 | 10.0 | 20.0 | 30.0 | 10.0 | — |
| Ex. 14 | 60.0 | 15.0 | 15.0 | 30.0 | 10.0 | — |
| Ex. 15 | 60.0 | 20.0 | 10.0 | 30.0 | 10.0 | — |
| Ex. 16 | 55.0 | 2.5 | 27.5 | 30.0 | 15.0 | — |
| Ex. 17 | 55.0 | 5.0 | 25.0 | 30.0 | 15.0 | — |
| Ex. 18 | 55.0 | 10.0 | 20.0 | 30.0 | 15.0 | — |
| Ex. 19 | 55.0 | 15.0 | 15.0 | 30.0 | 15.0 | — |
| Ex. 20 | 55.0 | 20.0 | 10.0 | 30.0 | 15.0 | — |
| Ex. 21 | 50.0 | 2.5 | 27.5 | 30.0 | 20.0 | — |
| Ex. 22 | 50.0 | 5.0 | 25.0 | 30.0 | 20.0 | — |
| Ex. 23 | 50.0 | 10.0 | 20.0 | 30.0 | 20.0 | — |
| Ex. 24 | 50.0 | 15.0 | 15.0 | 30.0 | 20.0 | — |
| Ex. 25 | 50.0 | 20.0 | 10.0 | 30.0 | 20.0 | — |
| Ex. 26 | 45.0 | 2.5 | 27.5 | 30.0 | 25.0 | — |
| Ex. 27 | 45.0 | 5.0 | 25.0 | 30.0 | 25.0 | — |
| Ex. 28 | 45.0 | 10.0 | 20.0 | 30.0 | 25.0 | — |
| Ex. 29 | 45.0 | 15.0 | 15.0 | 30.0 | 25.0 | — |
| Ex. 30 | 45.0 | 20.0 | 10.0 | 30.0 | 25.0 | — |
| Comp. Ex. 6 | 60.0 | 10.0 | 20.0 | 30.0 | — | XPVP 10.0 |
| Comp. Ex. 7 | 60.0 | 10.0 | 20.0 | 30.0 | — | $SiO_2$ 10.0 |
| Comp. Ex. 8 | 60.0 | 10.0 | 20.0 | 30.0 | — | HT 10.0 | note)
The unit of the numerical values is wt % relative to the total weight of the adhesive layer.

TABLE 2

Results of adhesive force test of Examples 1-30, Comparative Examples 1-5 in Table 1

| | organic fluid component having high polarity PGML (angle on organic conceptual diagram 28°) | | | | |
|---|---|---|---|---|---|
| Neusilin | 2.5 | 5.0 | 10.0 | 15.0 | 20.0 |
| 0 | ⊙ | ○ | Δ | Δ | Δ |
| 2.5 | ⊙ | ⊙ | not measured | Δ | Δ |
| 5.0 | ⊙⊙ | ⊙⊙ | ○○ | ΔΔ | Δ |
| 10.0 | ⊙⊙ | ⊙⊙ | ○○ | ΔΔ | Δ |
| 15.0 | ⊙⊙ | ⊙⊙ | ○○ | ΔΔ | Δ |
| 20.0 | ⊙⊙ | ⊙⊙ | not measured | ΔΔ | Δ |

TABLE 3

Results of adhesive force test of Comparative Examples 6-8 in Table 1

| — | adhesive | organic fluid component having high polarity PGML | powder | adhesive force |
|---|---|---|---|---|
| Comp. Ex. 6 | 60.0 | 10.0 | XPVP 10.0 | ΔΔΔ |
| Comp. Ex. 7 | 60.0 | 10.0 | SiO$_2$ 10.0 | Δ |
| Comp. Ex. 8 | 60.0 | 10.0 | HT 10.0 | Δ | note)
The unit of the numerical values is wt % relative to the total weight of the adhesive layer.

From Tables 2, 3, it is clear that the adhesive force of the adhesive layer is improved by adding Neusilin to the adhesive layer containing PGML (angle on organic conceptual diagram 28°) as an organic fluid component having high polarity, and addition of a powder other than Neusilin to the adhesive layer does not improve the adhesive force of the adhesive layer or, even if the adhesive force of the adhesive layer is improved, the improving effect thereof is inferior to that of Neusilin.

Examples 31-60 and Comparative Examples 9-16

Using Tween80 (angle on organic conceptual diagram 56°) as an organic fluid component having high polarity and according to the compounding ratios described in Table 4, a solution of the composition for forming an adhesive layer in toluene was prepared, the obtained solution was applied onto a poly(ethylene terephthalate) (PET) liner (thickness 75 μm) that underwent a silicone peel treatment such that the thickness after drying was 60 μm, and dried in a hot air circulation type drying device at 100° C. for 3 min to form an adhesive layer. The adhesive layer was adhered to a support made from PET to give a sheet-like patch. The obtained patch was subjected to the above-mentioned adhesive force test.

TABLE 4

Tween80 (angle on organic conceptual diagram 56°) was used as organic fluid component having high polarity

| | | organic fluid components | | | powder | |
|---|---|---|---|---|---|---|
| — | adhesive | organic fluid component having high polarity Tween80 | organic fluid component having low polarity IPM | total amount of organic fluid component | magnesium alumino-metasilicate (Neusilin) | other powder |
| Comp. Ex. 9 | 70.0 | 2.5 | 27.5 | 30.0 | 0.0 | — |
| Comp. Ex. 10 | 70.0 | 5.0 | 25.0 | 30.0 | 0.0 | — |
| Comp. Ex. 11 | 70.0 | 10.0 | 20.0 | 30.0 | 0.0 | — |
| Comp. Ex. 12 | 70.0 | 15.0 | 15.0 | 30.0 | 0.0 | — |
| Comp. Ex. 13 | 70.0 | 20.0 | 10.0 | 30.0 | 0.0 | — |
| Ex. 31 | 67.5 | 2.5 | 27.5 | 30.0 | 2.5 | — |
| Ex. 32 | 67.5 | 5.0 | 25.0 | 30.0 | 2.5 | — |
| Ex. 33 | 67.5 | 10.0 | 20.0 | 30.0 | 2.5 | — |
| Ex. 34 | 67.5 | 15.0 | 15.0 | 30.0 | 2.5 | — |
| Ex. 35 | 67.5 | 20.0 | 10.0 | 30.0 | 2.5 | — |
| Ex. 36 | 65.0 | 2.5 | 27.5 | 30.0 | 5.0 | — |
| Ex. 37 | 65.0 | 5.0 | 25.0 | 30.0 | 5.0 | — |

TABLE 4-continued

Tween80 (angle on organic conceptual diagram 56°)
was used as organic fluid component having high polarity

| | | organic fluid components | | | powder | |
|---|---|---|---|---|---|---|
| — | adhesive | organic fluid component having high polarity Tween80 | organic fluid component having low polarity IPM | total amount of organic fluid component | magnesium alumino-metasilicate (Neusilin) | other powder |
| Ex. 38 | 65.0 | 10.0 | 20.0 | 30.0 | 5.0 | — |
| Ex. 39 | 65.0 | 15.0 | 15.0 | 30.0 | 5.0 | — |
| Ex. 40 | 65.0 | 20.0 | 10.0 | 30.0 | 5.0 | — |
| Ex. 41 | 60.0 | 2.5 | 27.5 | 30.0 | 10.0 | — |
| Ex. 42 | 60.0 | 5.0 | 25.0 | 30.0 | 10.0 | — |
| Ex. 43 | 60.0 | 10.0 | 20.0 | 30.0 | 10.0 | — |
| Ex. 44 | 60.0 | 15.0 | 15.0 | 30.0 | 10.0 | — |
| Ex. 45 | 60.0 | 20.0 | 10.0 | 30.0 | 10.0 | — |
| Ex. 46 | 55.0 | 2.5 | 27.5 | 30.0 | 15.0 | — |
| Ex. 47 | 55.0 | 5.0 | 25.0 | 30.0 | 15.0 | — |
| Ex. 48 | 55.0 | 10.0 | 20.0 | 30.0 | 15.0 | — |
| Ex. 49 | 55.0 | 15.0 | 15.0 | 30.0 | 15.0 | — |
| Ex. 50 | 55.0 | 20.0 | 10.0 | 30.0 | 15.0 | — |
| Ex. 51 | 55.0 | 2.5 | 27.5 | 30.0 | 20.0 | — |
| Ex. 52 | 55.0 | 5.0 | 25.0 | 30.0 | 20.0 | — |
| Ex. 53 | 55.0 | 10.0 | 20.0 | 30.0 | 20.0 | — |
| Ex. 54 | 55.0 | 15.0 | 15.0 | 30.0 | 20.0 | — |
| Ex. 55 | 55.0 | 20.0 | 10.0 | 30.0 | 20.0 | — |
| Ex. 56 | 55.0 | 2.5 | 27.5 | 30.0 | 25.0 | — |
| Ex. 57 | 55.0 | 5.0 | 25.0 | 30.0 | 25.0 | — |
| Ex. 58 | 55.0 | 10.0 | 20.0 | 30.0 | 25.0 | — |
| Ex. 59 | 55.0 | 15.0 | 15.0 | 30.0 | 25.0 | — |
| Ex. 60 | 55.0 | 20.0 | 10.0 | 30.0 | 25.0 | — |
| Comp. Ex. 14 | 60.0 | 10.0 | 20.0 | 30.0 | — | XPVP 10.0 |
| Comp. Ex. 15 | 60.0 | 10.0 | 20.0 | 30.0 | — | SiO$_2$ 10.0 |
| Comp. Ex. 16 | 60.0 | 10.0 | 20.0 | 30.0 | — | HT 10.0 | note)
The unit of the numerical values is wt % relative to the total weight of the adhesive layer.

TABLE 5

Results of adhesive force test of Examples 31-60
and Comparative Examples 9-13 in Table 4

| | organic fluid component having high polarity Tween80 (angle on organic conceptual diagram 56°) | | | | |
|---|---|---|---|---|---|
| Neusilin | 2.5 | 5.0 | 10.0 | 15.0 | 20.0 |
| 0 | Δ | Δ | Δ | Δ | Δ |
| 2.5 | ◯ | Δ | Δ | Δ | Δ |
| 5.0 | ⊙⊙ | ◯◯ | not measured | Δ | Δ |
| 10.0 | ⊙⊙ | ⊙⊙ | ⊙⊙ | ◯ | Δ |
| 15.0 | ⊙⊙ | ⊙⊙ | ⊙⊙ | ⊙ | ⊙ |
| 20.0 | ⊙⊙ | ⊙⊙ | ⊙⊙ | Δ | X |

TABLE 6

Results of adhesive force test of Comparative
Examples 14-16 in Table 4

| — | adhesive | organic fluid component having high polarity Tween80 | powder | adhesive force |
|---|---|---|---|---|
| Comp. Ex. 14 | 60.0 | 10.0 | XPVP 10.0 | ΔΔ |
| Comp. Ex. 15 | 60.0 | 10.0 | SiO$_2$ 10.0 | Δ |
| Comp. Ex. 16 | 60.0 | 10.0 | HT 10.0 | Δ |

From Tables 5, 6, it is clear that the adhesive force of the adhesive layer is improved by adding Neusilin to the adhesive layer containing Tween80 as an organic fluid component having high polarity, and addition of a powder other than Neusilin to the adhesive layer does not improve the adhesive force of the adhesive layer or, even if the adhesive force of the adhesive layer is improved, the improving effect thereof is inferior to that of Neusilin.

Examples 61-90 and Comparative Examples 17-24

Using Glycerin (angle on organic conceptual diagram 79°) as an organic fluid component having high polarity and according to the compounding ratios described in Table 7, a solution of the composition for forming an adhesive layer in toluene was prepared. As for glycerin, a 30% isopropanol solution was prepared and added. The obtained solution was applied onto a poly(ethylene terephthalate) (PET) liner (thickness 75 μm) that underwent a silicone peel treatment such that the thickness after drying was 60 μm, and dried in a hot air circulation type drying device at 100° C. for 3 min to form an adhesive layer. The adhesive layer was adhered to a support made from PET to give a sheet-like patch. The obtained patch was subjected to the above-mentioned adhesive force test.

TABLE 7

Glycerin (angle on organic conceptual diagram 79°) was used as organic fluid component having high polarity

| | | total amount of organic fluid component | | | powder | |
|---|---|---|---|---|---|---|
| — | adhesive | organic fluid component having high polarity Glycerin | organic fluid component having low polarity IPM | total amount of organic fluid component | magnesium alumino-metasilicate (Neusilin) | other powder |
| Comp. Ex. 17 | 70.0 | 2.5 | 27.5 | 30.0 | 0.0 | — |
| Comp. Ex. 18 | 70.0 | 5.0 | 25.0 | 30.0 | 0.0 | — |
| Comp. Ex. 19 | 70.0 | 10.0 | 20.0 | 30.0 | 0.0 | — |
| Comp. Ex. 20 | 70.0 | 15.0 | 15.0 | 30.0 | 0.0 | — |
| Comp. Ex. 21 | 70.0 | 20.0 | 10.0 | 30.0 | 0.0 | — |
| Ex. 61 | 67.5 | 2.5 | 27.5 | 30.0 | 2.5 | — |
| Ex. 62 | 67.5 | 5.0 | 25.0 | 30.0 | 2.5 | — |
| Ex. 63 | 67.5 | 10.0 | 20.0 | 30.0 | 2.5 | — |
| Ex. 64 | 67.5 | 15.0 | 15.0 | 30.0 | 2.5 | — |
| Ex. 65 | 67.5 | 20.0 | 10.0 | 30.0 | 2.5 | — |
| Ex. 66 | 65.0 | 2.5 | 27.5 | 30.0 | 5.0 | — |
| Ex. 67 | 65.0 | 5.0 | 25.0 | 30.0 | 5.0 | — |
| Ex. 68 | 65.0 | 10.0 | 20.0 | 30.0 | 5.0 | — |
| Ex. 69 | 65.0 | 15.0 | 15.0 | 30.0 | 5.0 | — |
| Ex. 70 | 65.0 | 20.0 | 10.0 | 30.0 | 5.0 | — |
| Ex. 71 | 60.0 | 2.5 | 27.5 | 30.0 | 10.0 | — |
| Ex. 72 | 60.0 | 5.0 | 25.0 | 30.0 | 10.0 | — |
| Ex. 73 | 60.0 | 10.0 | 20.0 | 30.0 | 10.0 | — |
| Ex. 74 | 60.0 | 15.0 | 15.0 | 30.0 | 10.0 | — |
| Ex. 75 | 60.0 | 20.0 | 10.0 | 30.0 | 10.0 | — |
| Ex. 76 | 55.0 | 2.5 | 27.5 | 30.0 | 15.0 | — |
| Ex. 77 | 55.0 | 5.0 | 25.0 | 30.0 | 15.0 | — |
| Ex. 78 | 55.0 | 10.0 | 20.0 | 30.0 | 15.0 | — |
| Ex. 79 | 55.0 | 15.0 | 15.0 | 30.0 | 15.0 | — |
| Ex. 80 | 55.0 | 20.0 | 10.0 | 30.0 | 15.0 | — |
| Ex. 81 | 55.0 | 2.5 | 27.5 | 30.0 | 20.0 | — |
| Ex. 82 | 55.0 | 5.0 | 25.0 | 30.0 | 20.0 | — |
| Ex. 83 | 55.0 | 10.0 | 20.0 | 30.0 | 20.0 | — |
| Ex. 84 | 55.0 | 15.0 | 15.0 | 30.0 | 20.0 | — |
| Ex. 85 | 55.0 | 20.0 | 10.0 | 30.0 | 20.0 | — |
| Ex. 86 | 55.0 | 2.5 | 27.5 | 30.0 | 25.0 | — |
| Ex. 87 | 55.0 | 5.0 | 25.0 | 30.0 | 25.0 | — |
| Ex. 88 | 55.0 | 10.0 | 20.0 | 30.0 | 25.0 | — |
| Ex. 89 | 55.0 | 15.0 | 15.0 | 30.0 | 25.0 | — |
| Ex. 90 | 55.0 | 20.0 | 10.0 | 30.0 | 25.0 | — |
| Comp. Ex. 22 | 65.0 | 10.0 | 20.0 | 30.0 | — | XPVP 5.0 |
| Comp. Ex. 23 | 65.0 | 10.0 | 20.0 | 30.0 | — | SiO$_2$ 5.0 |
| Comp. Ex. 24 | 65.0 | 10.0 | 20.0 | 30.0 | — | HT 5.0 | note)
The unit of the numerical values is wt % relative to the total weight of the adhesive layer.

TABLE 8

Results of adhesive force test of Examples 61-90 and Comparative Examples 17-21 in Table 7

| | organic fluid component having high polarity Glycerine (angle on organic conceptual diagram 79°) | | | | |
|---|---|---|---|---|---|
| Neusilin | 2.5 | 5.0 | 10.0 | 15.0 | 20.0 |
| 0 | XX | XX | XX | XX | XX |
| 2.5 | ⊙⊙ | ⊙⊙ | XX | XX | XX |
| 5.0 | ⊙⊙ | ⊙⊙ | ⊙⊙ | ⊙⊙ | XX |
| 10.0 | ⊙⊙ | ⊙⊙ | ⊙⊙ | ⊙⊙ | XX |
| 15.0 | ⊙⊙ | ⊙⊙ | ⊙⊙ | ⊙⊙ | XX |
| 20.0 | ⊙ | ⊙ | ⊙ | ⊙ | XX |

TABLE 9

Results of adhesive force test of Comparative Examples 22-24 in Table 7

| — | adhesive | organic fluid component having high polarity Glycerin | powder | adhesive force |
|---|---|---|---|---|
| Comp. Ex. 22 | 60.0 | 10.0 | XPVP 5.0 | XX |
| Comp. Ex. 23 | 60.0 | 10.0 | SiO$_2$ 5.0 | XX |
| Comp. Ex. 24 | 60.0 | 10.0 | HT 5.0 | XX |

As shown in Table 8, the composition for forming an adhesive layer, which contained Glycerin as an organic fluid component having high polarity (angle on organic conceptual diagram 79°) showed separation of glycerin in the toluene solution, and a uniform adhesive layer could not be prepared. However, when it contained not less than 2.5% of Neusilin, a uniform adhesive layer could be prepared and the adhesive force became high. As shown in Table 9, a powder other than Neusilin failed to form a uniform adhesive layer due to the coagulation of powder or separation of Glycerin in the toluene solution of the composition for forming an adhesive layer.

<Patch Preparation>

Patch preparations are produced in the same manner as in the above-mentioned Examples except that 1 part by weight of the adhesive in the adhesive layer of the patch is replaced by 1 part by weight of indomethacin or ibandronic acid as a drug.

Such patch preparations have properties similar to those of the patch in each Example.

The angles (angle on organic conceptual diagram) of the above-mentioned drugs calculated from the inorganic value and organic value in the organic conceptual diagram are as follows.

indomethacin 44°
ibandronic acid 77°

INDUSTRIAL APPLICABILITY

According to the present invention, a patch and a patch preparation, which can prevent blooming of an organic fluid component having high polarity on an adhesive layer surface, and afford sufficiently high adhesive force, even if they contain a highly hydrophobic adhesive such as synthetic rubber together with an organic fluid component having high polarity which is less compatible with the synthetic rubber, can be realized.

This application is based on a patent application No. 2011-021200 filed in Japan, the contents of which are incorporated in full herein.

The invention claimed is:

1. A patch comprising a support and an adhesive layer on at least one surface of the support, wherein the adhesive layer comprises poly(2-methylpropene) having a viscosity average molecular weight of 4,000,000-6,500,000, an organic fluid component having high polarity, a tackifier, and magnesium aluminometasilicate, wherein the magnesium aluminometasilicate comprises an amorphous composite oxide of the formula:

$$Al_2O_3/aMgO/bSiO_2 \cdot nH_2O,$$

wherein a is 0.3-3 and b is 0.3-5, the total content of magnesium aluminometasilicate in the adhesive layer is less than 25 wt % relative to the total weight of the adhesive layer, and the organic fluid component having high polarity has an angle within the range of 20°-80° as calculated by the following formula using an inorganic value and an organic value in an organic conceptual diagram:

$$\text{Angle}[°] = \text{arc tan}(\text{organic value}/\text{inorganic value})^{-1} \times (180/\pi).$$

2. The patch according to claim 1, wherein the content of the organic fluid component having high polarity in the adhesive layer is not more than 20 wt % relative to the total weight of the adhesive layer.

3. The patch according to claim 1, further comprising an organic fluid component having low polarity which shows lower polarity than the organic fluid component having high polarity, wherein the organic fluid component having low polarity has an angle within the range of 0°-19° as calculated by the following formula and using an inorganic value and an organic value in an organic conceptual diagram:

$$\text{Angle}[°] = \text{arc tan}(\text{organic value}/\text{inorganic value})^{-1} \times (180/\pi).$$

4. The patch according to claim 3, wherein the total content of the organic fluid component having high polarity and the organic fluid component having low polarity in the adhesive layer is not more than 50 wt % relative to the total weight of the adhesive layer.

5. A patch preparation further comprising a drug in the adhesive layer of the patch according to claim 1.

6. A patch preparation further comprising a drug in the adhesive layer of the patch according to claim 2.

7. A patch preparation further comprising a drug in the adhesive layer of the patch according to claim 3.

8. A patch preparation further comprising a drug in the adhesive layer of the patch according to claim 4.

* * * * *